United States Patent
Georges et al.

(10) Patent No.: US 9,180,022 B2
(45) Date of Patent: Nov. 10, 2015

(54) SPINAL ALIGNMENT CLIP

(71) Applicants: Bacem Georges, Franklin, MA (US); Thomas Gamache, Westport, MA (US); Carl Legge, Raynham, MA (US); Glen Presbrey, Mapleville, MA (US)

(72) Inventors: Bacem Georges, Franklin, MA (US); Thomas Gamache, Westport, MA (US); Carl Legge, Raynham, MA (US); Glen Presbrey, Mapleville, MA (US)

(73) Assignee: DePuy Synthes Products, Inc., Raynham, MA (US)

( * ) Notice: Subject to any disclaimer, the term of this patent is extended or adjusted under 35 U.S.C. 154(b) by 314 days.

(21) Appl. No.: 13/929,936

(22) Filed: Jun. 28, 2013

(65) Prior Publication Data

US 2015/0005879 A1 Jan. 1, 2015

(51) Int. Cl.
*A61F 2/44* (2006.01)
*A61B 17/70* (2006.01)
*A61B 17/80* (2006.01)

(52) U.S. Cl.
CPC ............. *A61F 2/447* (2013.01); *A61B 17/7059* (2013.01); *A61B 17/808* (2013.01)

(58) Field of Classification Search
CPC ................................ A61B 17/7059; A61F 2/447
See application file for complete search history.

(56) References Cited

U.S. PATENT DOCUMENTS

| | | | |
|---|---|---|---|
| 5,443,514 A * | 8/1995 | Steffee ........................... 128/898 |
| 5,989,289 A * | 11/1999 | Coates et al. ............... 623/17.16 |
| 6,102,950 A * | 8/2000 | Vaccaro ...................... 623/17.16 |
| 6,156,037 A * | 12/2000 | LeHuec et al. ................. 606/247 |
| 6,235,059 B1 * | 5/2001 | Benezech et al. ........... 623/17.16 |
| 6,602,257 B1 * | 8/2003 | Thramann .................... 606/86 B |
| 6,837,905 B1 * | 1/2005 | Lieberman ................. 623/17.16 |
| 7,172,627 B2 * | 2/2007 | Fiere et al. .................. 623/17.11 |
| 8,216,312 B2 * | 7/2012 | Gray .......................... 623/17.11 |
| 8,641,765 B2 * | 2/2014 | Muhanna ................... 623/17.16 |
| 8,840,667 B1 * | 9/2014 | Tumialan ................... 623/17.11 |
| 9,039,775 B2 * | 5/2015 | Fraser et al. ............... 623/17.16 |
| 2001/0049560 A1 * | 12/2001 | Paul et al. .................. 623/17.16 |
| 2002/0107572 A1 * | 8/2002 | Foley et al. ................ 623/17.11 |
| 2002/0169508 A1 * | 11/2002 | Songer et al. ............. 623/17.11 |
| 2005/0071008 A1 * | 3/2005 | Kirschman ................. 623/17.11 |
| 2005/0177245 A1 * | 8/2005 | Leatherbury et al. ........ 623/23.5 |
| 2006/0074488 A1 * | 4/2006 | Abdou ....................... 623/17.11 |
| 2007/0270965 A1 * | 11/2007 | Ferguson ................... 623/17.11 |
| 2008/0161925 A1 * | 7/2008 | Brittan et al. ............. 623/17.16 |
| 2008/0249569 A1 * | 10/2008 | Waugh et al. ................ 606/249 |
| 2010/0168798 A1 * | 7/2010 | Clineff et al. ................ 606/279 |
| 2010/0249937 A1 * | 9/2010 | Blain et al. ................ 623/17.16 |
| 2011/0144755 A1 * | 6/2011 | Baynham et al. .......... 623/17.16 |
| 2011/0190892 A1 * | 8/2011 | Kirschman ................ 623/17.16 |
| 2012/0078310 A1 * | 3/2012 | Bernstein ...................... 606/279 |
| 2012/0226319 A1 * | 9/2012 | Armstrong et al. ........... 606/279 |
| 2013/0060337 A1 * | 3/2013 | Petersheim et al. ....... 623/17.16 |
| 2013/0238095 A1 * | 9/2013 | Pavento et al. ............ 623/17.16 |
| 2014/0039623 A1 * | 2/2014 | Iott et al. ................... 623/17.16 |
| 2014/0107785 A1 * | 4/2014 | Geisler et al. ............. 623/17.16 |
| 2014/0107786 A1 * | 4/2014 | Geisler et al. ............. 623/17.16 |
| 2014/0114415 A1 * | 4/2014 | Tyber ........................ 623/17.16 |
| 2014/0200670 A1 * | 7/2014 | Chin et al. ................. 623/17.16 |
| 2014/0228958 A1 * | 8/2014 | Niemiec et al. ............ 623/17.16 |
| 2014/0371859 A1 * | 12/2014 | Petersheim et al. ....... 623/17.16 |
| 2015/0025635 A1 * | 1/2015 | Laubert ..................... 623/17.16 |

* cited by examiner

*Primary Examiner* — Christian Sevilla
(74) *Attorney, Agent, or Firm* — Raymond N. Scott, Jr.

(57) ABSTRACT

An instrument system for performing spinal surgery that helps provide optimal plate selection as well as an improved temporary alignment and retention means, without the need to penetrate the vertebral bodies with temporary fixation pins. The instrument system of the present invention has a clip that possesses features that temporarily center, align and position the plate to the interbody cage. This clip mates with the cage by hugging the outside parameters of the cage, as well as within the window (central through-hole) of the cervical plate.

18 Claims, 21 Drawing Sheets

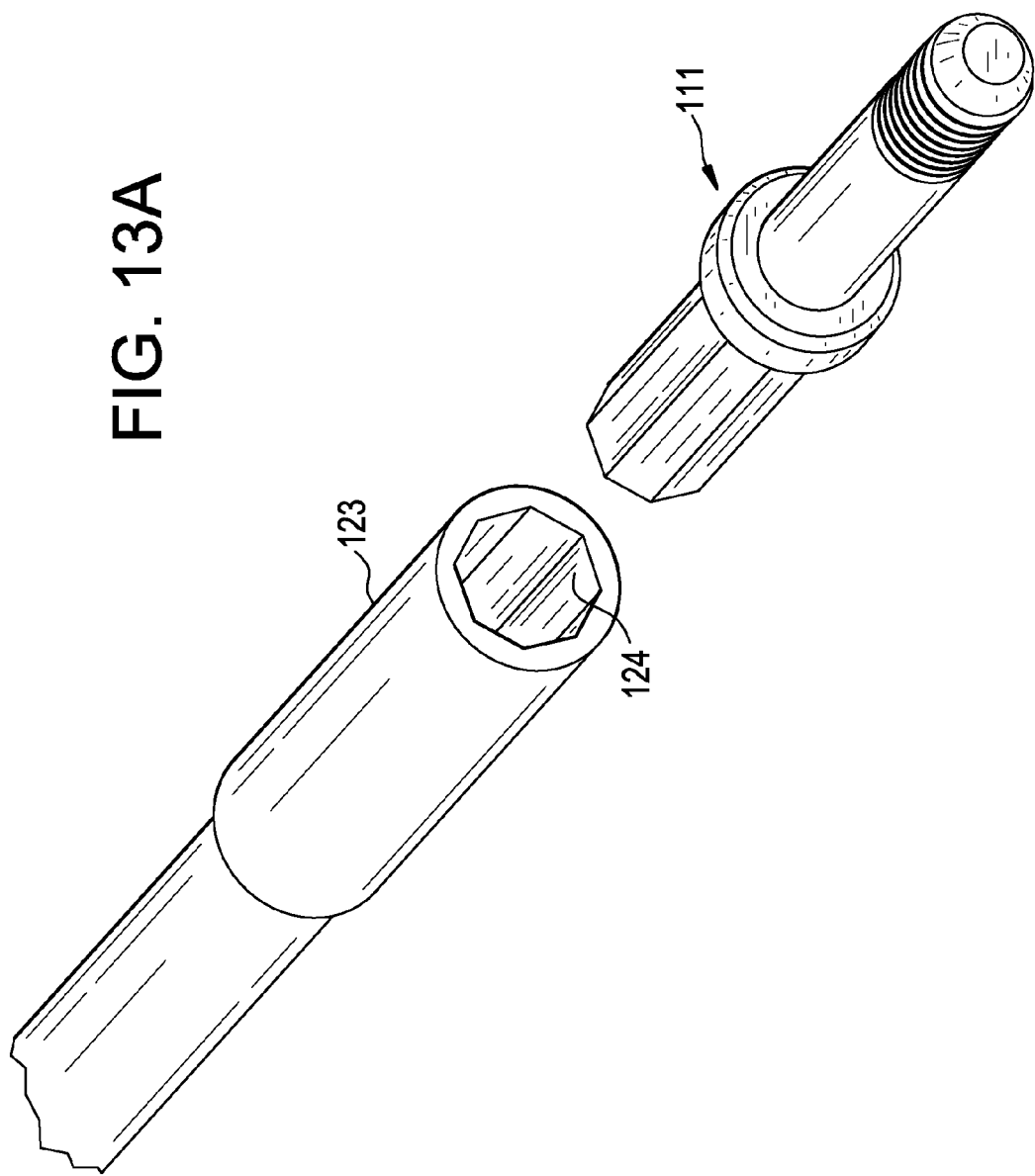

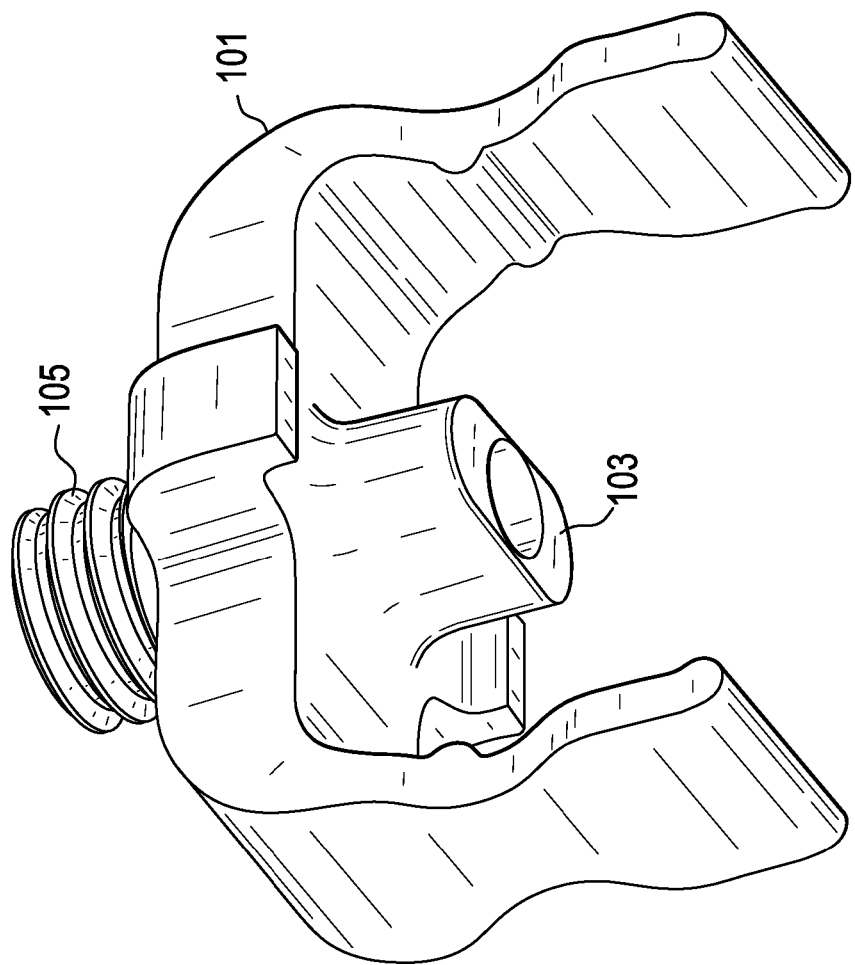

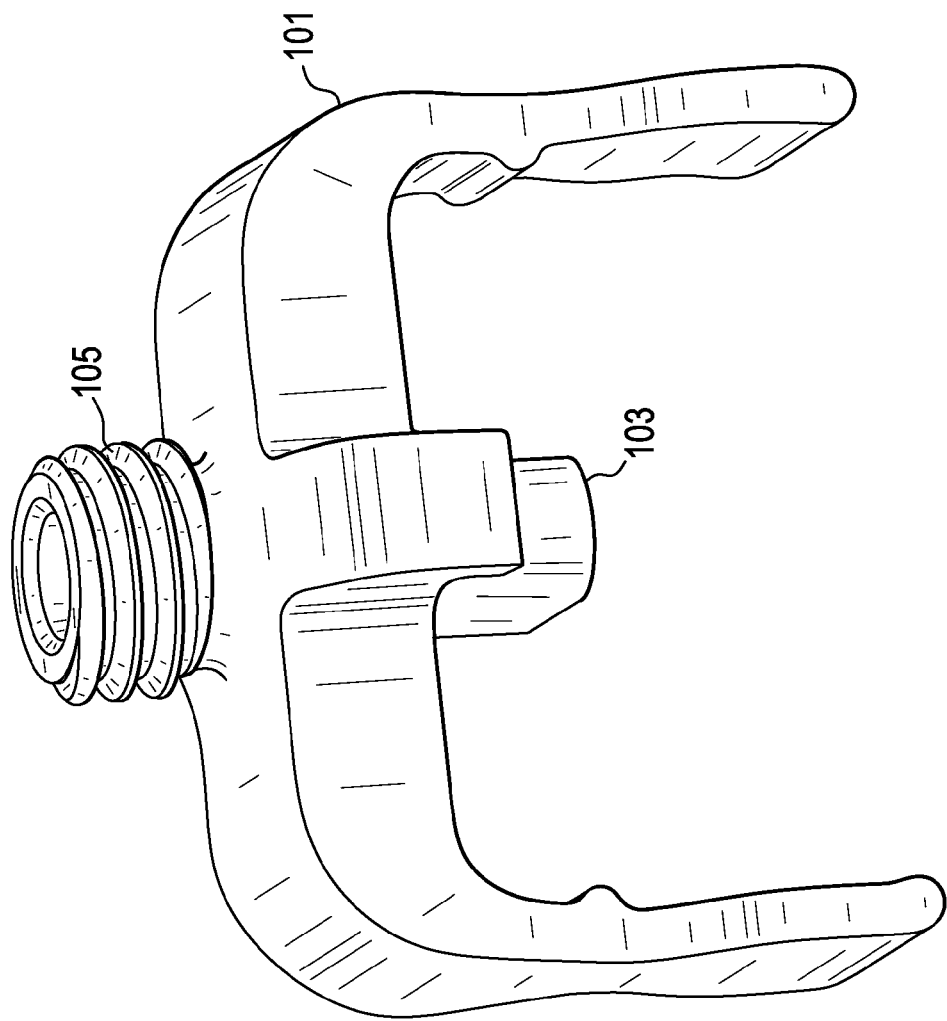

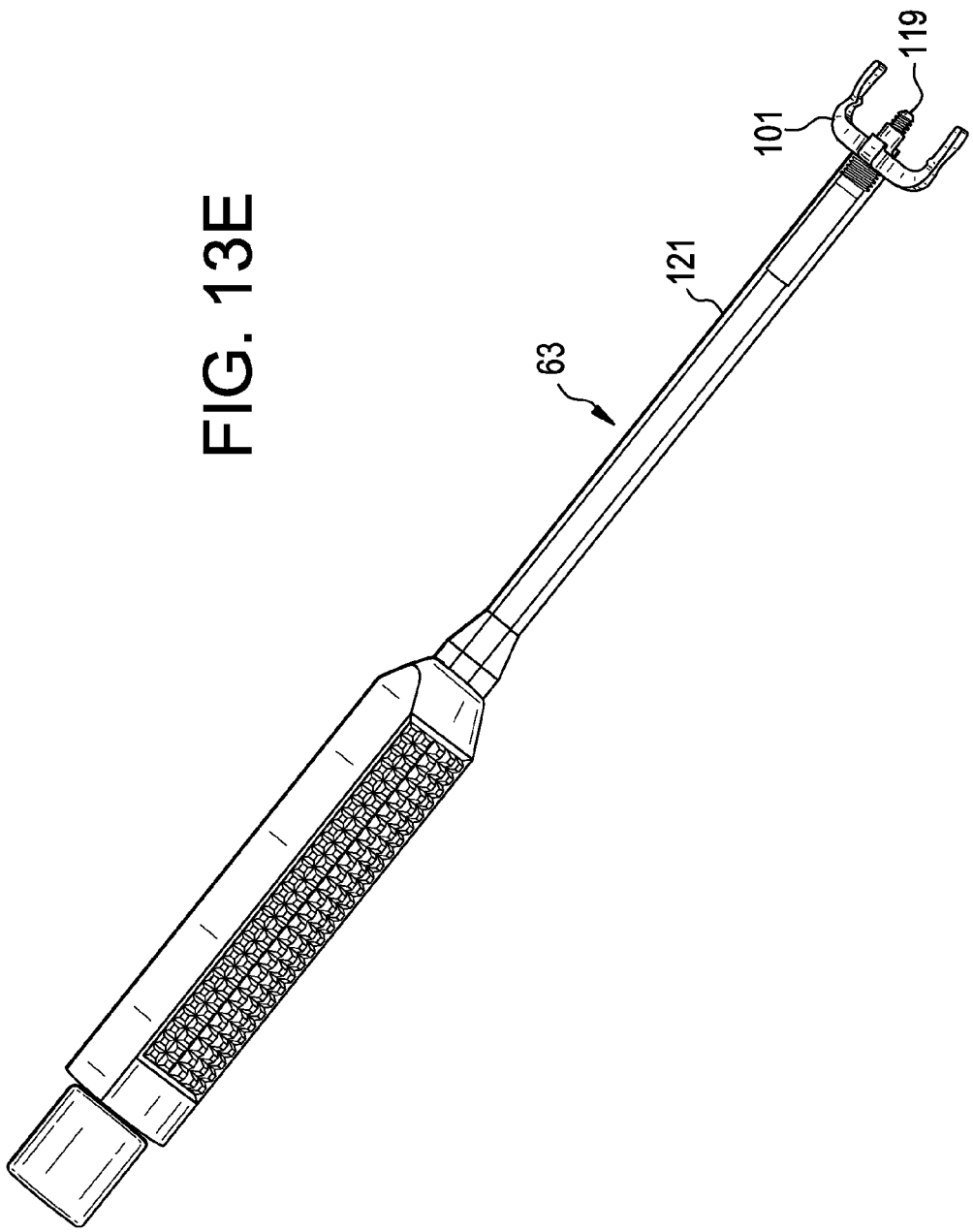

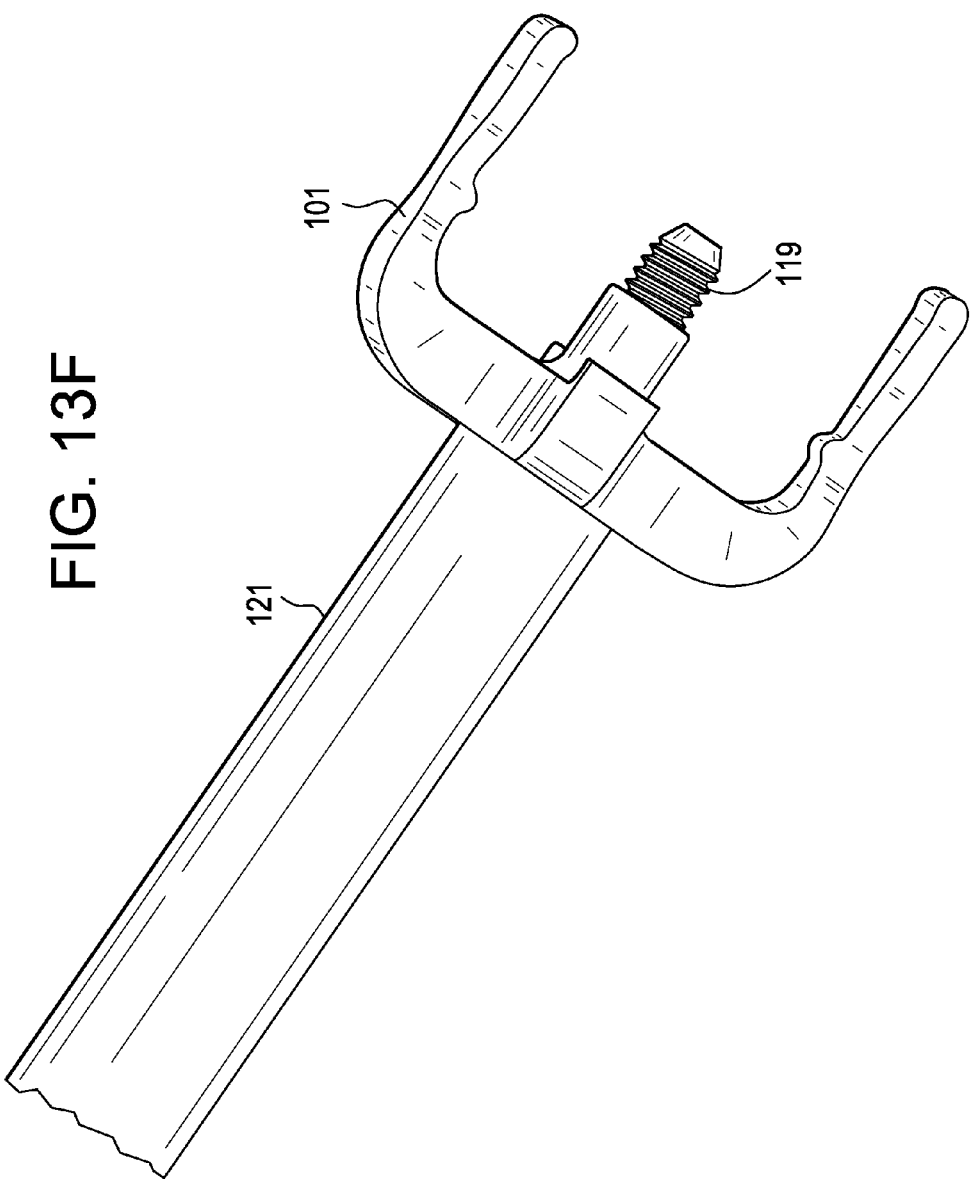

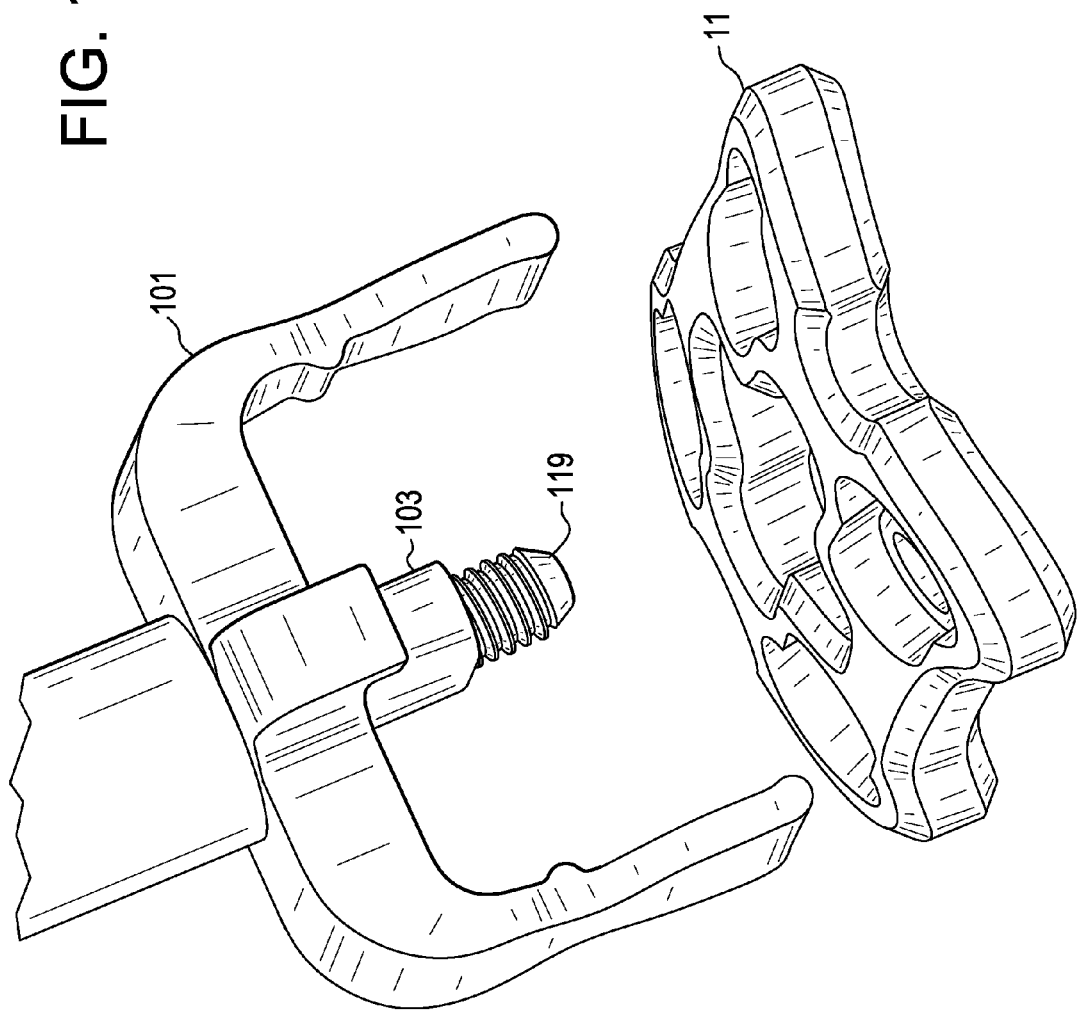

A # SPINAL ALIGNMENT CLIP

BACKGROUND OF THE INVENTION

After performing an anterior- or lateral-approach discectomy and then inserting an intervetebral spacer/cage/bone strut into a disc space, some spine surgeons prefer not to insert a plate onto the outer surface of the bone and then add fixation through the face of the cephalad and caudal vertebral bodies without first checking the relative alignment of the plate to the surrounding anatomy and endplates. Often times, the plate can be considered to be malpositioned when viewed under x-ray. The malpositioning can be attributed to no consistent effective means of ensuring that the plate is aligned to the cage through pure visualization of the plate within the retracted tissue.

Instead, the current standard of care is to penetrate the cephalad and caudal vertebral bodies using temporary fixations pins through a feature of the plate to temporarily secure the plate in what the surgeons approximates to be perpendicular to the disc space and cage. Once the plate is temporarily secured, the surgeon may or may not release retraction and bring in the x-ray equipment (C-ARM) to take a few anterior-posterior x-rays using the best alignment methods they can by eye with again consideration for the patient's alignment on the table and the pathology they are treating. An x-ray that is erroneously taken slightly off axis (z-axis) can give the surgeon a false impression that the plate is aligned in the ideal location, leading to securement of the plate in what is believed to be an ideal spot, even though it may be malpositioned. Conversely, a surgeon may also get a false impression that the plate is not aligned ideally. This occurs when the plate is in the ideal position but the C-arm is off axis.

A malpositioned plate may sometimes cause patient discomfort and clinical issues like dysphasia/dysphonia in the cervical spine, or adjacent level degradation and tissue irritation in all areas of the spine. Additionally, the bio-mechanics of the plate and the surrounding non fused levels may not be preserved if the plate is malpositioned. Malpositioned plates can contribute to higher likelihood of revision operations. In addition, incorrect selection of plates (i.e., excessively long plates) can result in increased revision surgeries . See, for example, Park, J. Bone Joint Surg., 87A, 3, Mar. 2005, 558-563.

US Patent Publication 2012-0078310 (Bernstein) discloses a device and method of application, combining a cervical plate system with a cervical graft (bone or synthetic) for the safe and efficient stabilization of the cervical spine. The application of a plate to the spine for fixation purposes is widely practiced. The present invention is designed to provide predictable, efficient, and safe fixation of the spine. The present invention is minimally invasive for the anatomical characteristics of the cervical bones or vertebrae. The present invention is designed primarily for use in the cervical spine, but can be applied to any level of application in the spinal column, including the thoracic and lumbo-sacral spine.

US Patent Publication 2012-0226319 (Warsaw Orthopedics) discloses Systems, methods and devices for providing stabilization between first and second vertebrae. More particularly, in one form a system includes an implant configured to be positioned in a disc space between the first and second vertebrae and a freestanding plate for engagement with extra-discal surfaces of the first and second vertebrae. The system also includes an insertion instrument with an engaging portion configured to releasably engage with the implant and the plate such that the implant and plate can be positioned together relative to the first and second vertebrae. In one aspect, an angular orientation of the implant relative to the plate is adjustable when the implant and the plate are engaged by the instrument. In this or another aspect, the implant and plate are held in a contiguous relationship when engaged by the instrument.

U.S. Pat. No. 7,648,511 (Spinecore I) discloses Instrumentation for implanting an intervertebral disc replacement device includes a drill guide comprising a shaft having a proximal end and a distal end and a guide member disposed at the distal end of the shaft and operable to engage an insertion plate that maintains first and second members of an intervertebral disc replacement device in registration with one another for insertion into an intervertebral disc space of a spinal column, wherein the guide member includes at least one guide bore operable to align with an area of a vertebral bone of the intervertebral disc space to which one of the first and second members of the intervertebral disc replacement device is to be attached.

US Patent Publication 2010-0070040 (Spinecore II) discloses instrumentation for implanting a cervical disc replacement device includes cervical disc replacement trials for determining the appropriate size of replacement device to be implanted, an insertion plate for maintaining the elements of the replacement device in fixed relation to one another for simultaneous manipulation, an insertion handle for attachment to the insertion plate for manipulation of the elements, an insertion pusher for releasing the insertion handle from the insertion plate, a drill guide that cooperates with the insertion plate to guide the drilling of tap holes for bone screws to be placed through bone screw holes in the flanges of the replacement device, clips that are applied to the flanges after placement of the bone screws to resist screw backout, and a clip applicator for applying the clips to the flanges.

SUMMARY OF THE INVENTION

The present invention relates to an instrument system for performing spinal surgery that helps provide optimal plate selection as well as an improved temporary alignment and retention means, without the need to penetrate the vertebral bodies with temporary fixation pins. The instrument system of the present invention has a clip that possesses features that temporarily center, align and position the plate to the interbody cage. This clip mates with the cage by hugging the lateral walls of the cage and by abutting the central window of the cervical plate. The clip can also act as a temporary fixation pin. It allows the surgeon to use any available drill guide with the cervical plate and even allows free handing of self-drilling screws without the use of any drill guide.

In some preferred embodiments, the instrument generally maintains a perpendicularity in the A/P plane relative to the implanted cage while allowing for cephalad/caudal translation of the plate. This design could also allow for a predetermined amount of micromotion and/or springback if desired. The instrument also will allow the cage to be recessed in the vertebral body (approximately up to 4 mm) and allow the plate to be positioned along the anatomical shape of the spine in the lateral plane.

In some preferred embodiments, the instrument generally maintains centering of the plate relative to the rotation of the proximal face of the cage, while allowing for poly-axial or preferably uni-axial rotation of the distal face of the plate to better mate with the anatomy. This temporary coupling and alignment allows for optimal placement of the cage without

DESCRIPTION OF THE FIGURES

FIGS. 13a-j disclose steps in a sequential insertion of the assembly into a disc space.

DETAILED DESCRIPTION OF THE INVENTION

Figure 1:
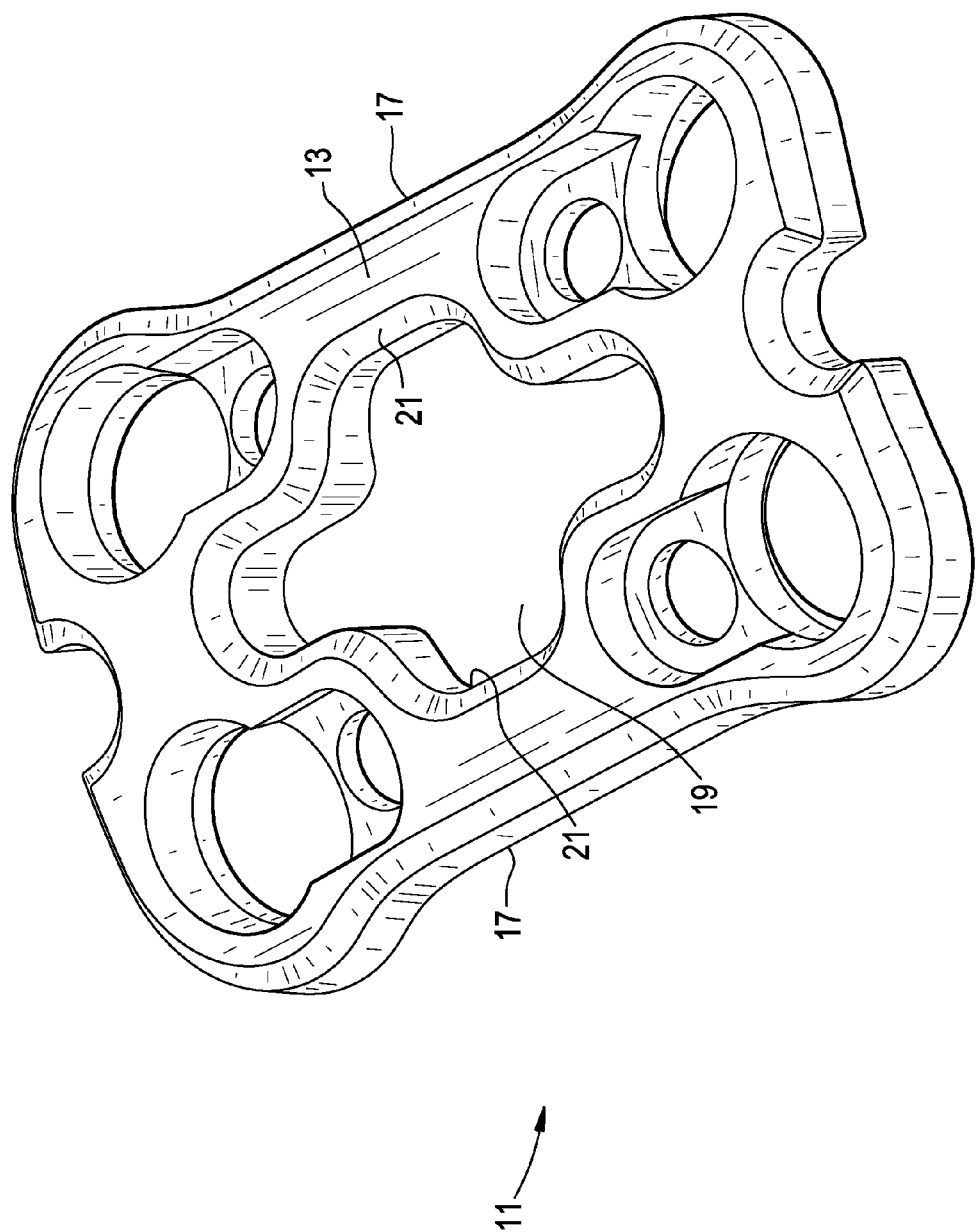
FIGS. 1 and 2 are perspective views of a plate component of the present invention.
Figure 2:
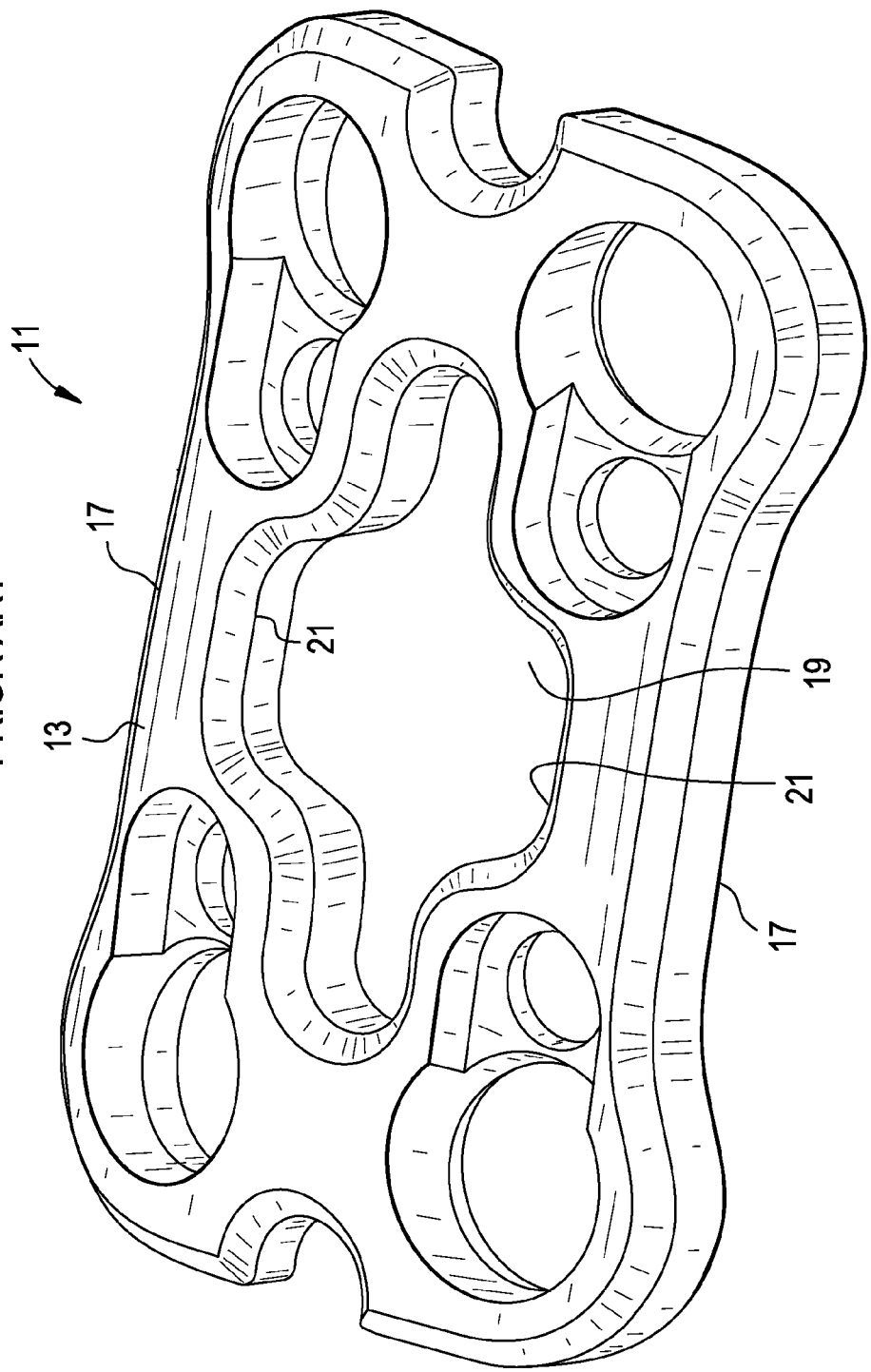
Figure 3:
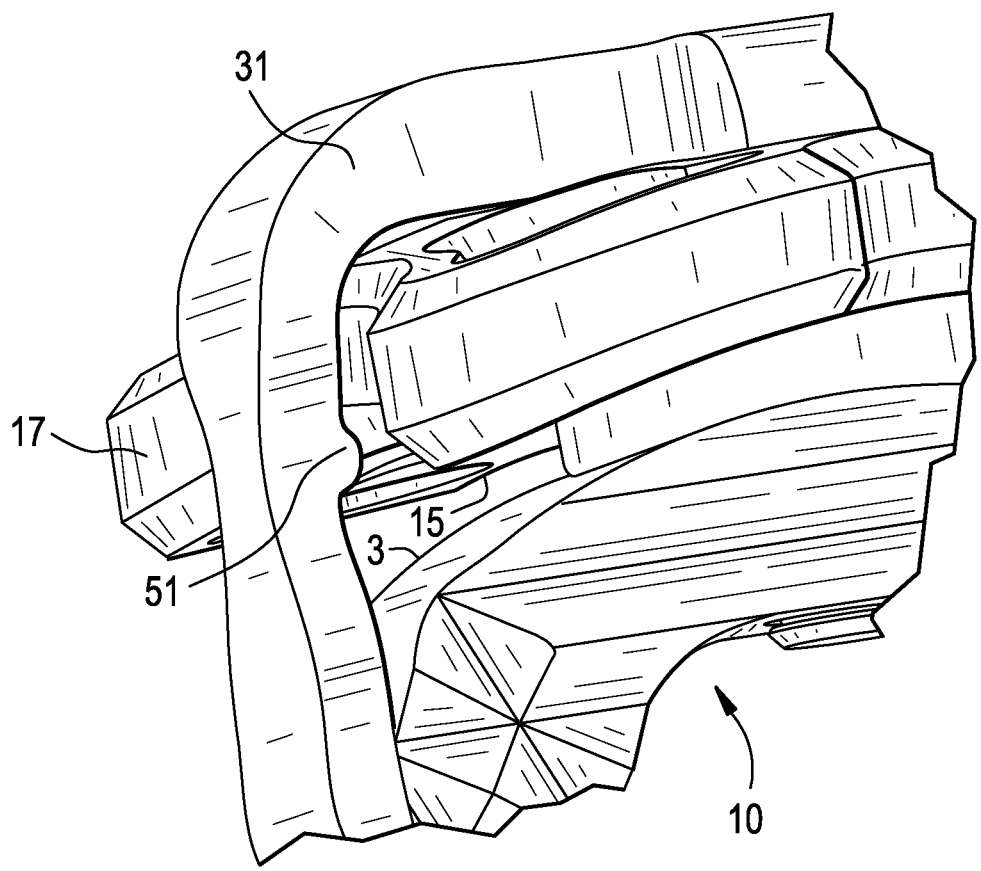
FIG. 3 is a close-up view of a portion of the assembly of the present invention, showing projection on one of the second pair of arms.
Figure 4:
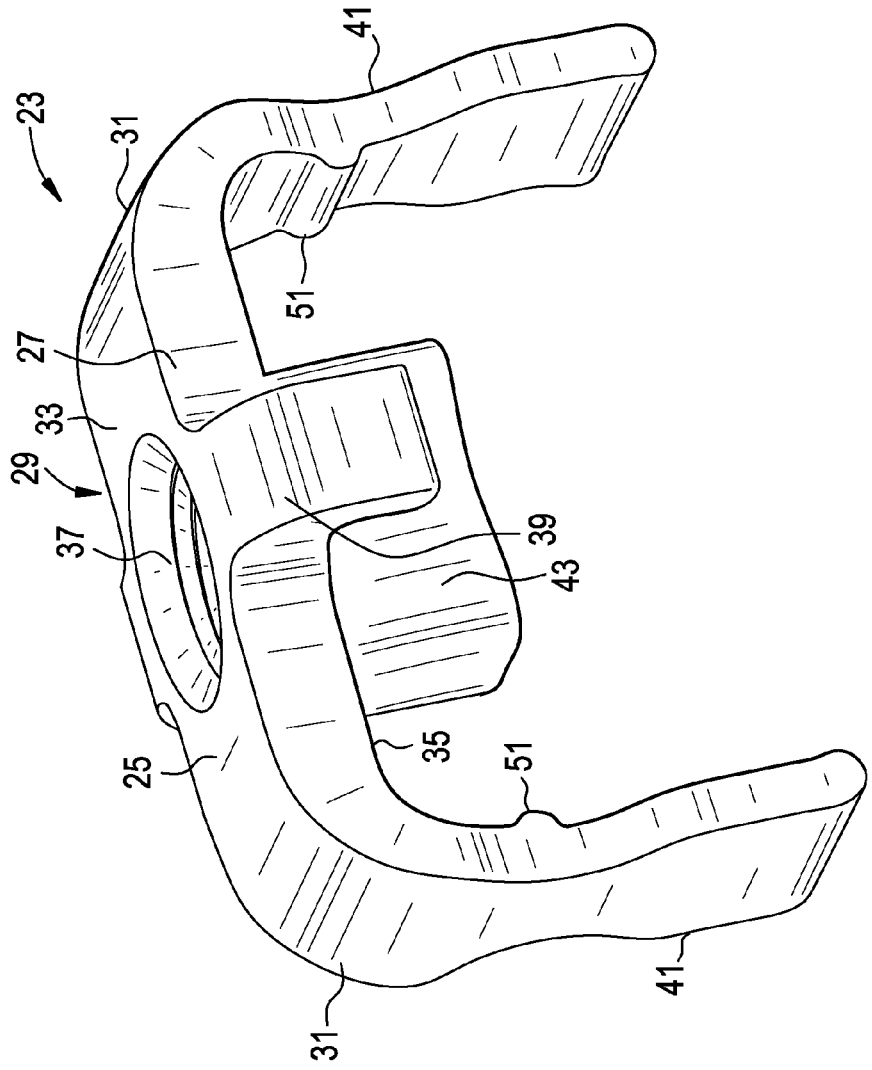
FIG. 4 is a perspective view of a clip of the present invention.
Figure 5:
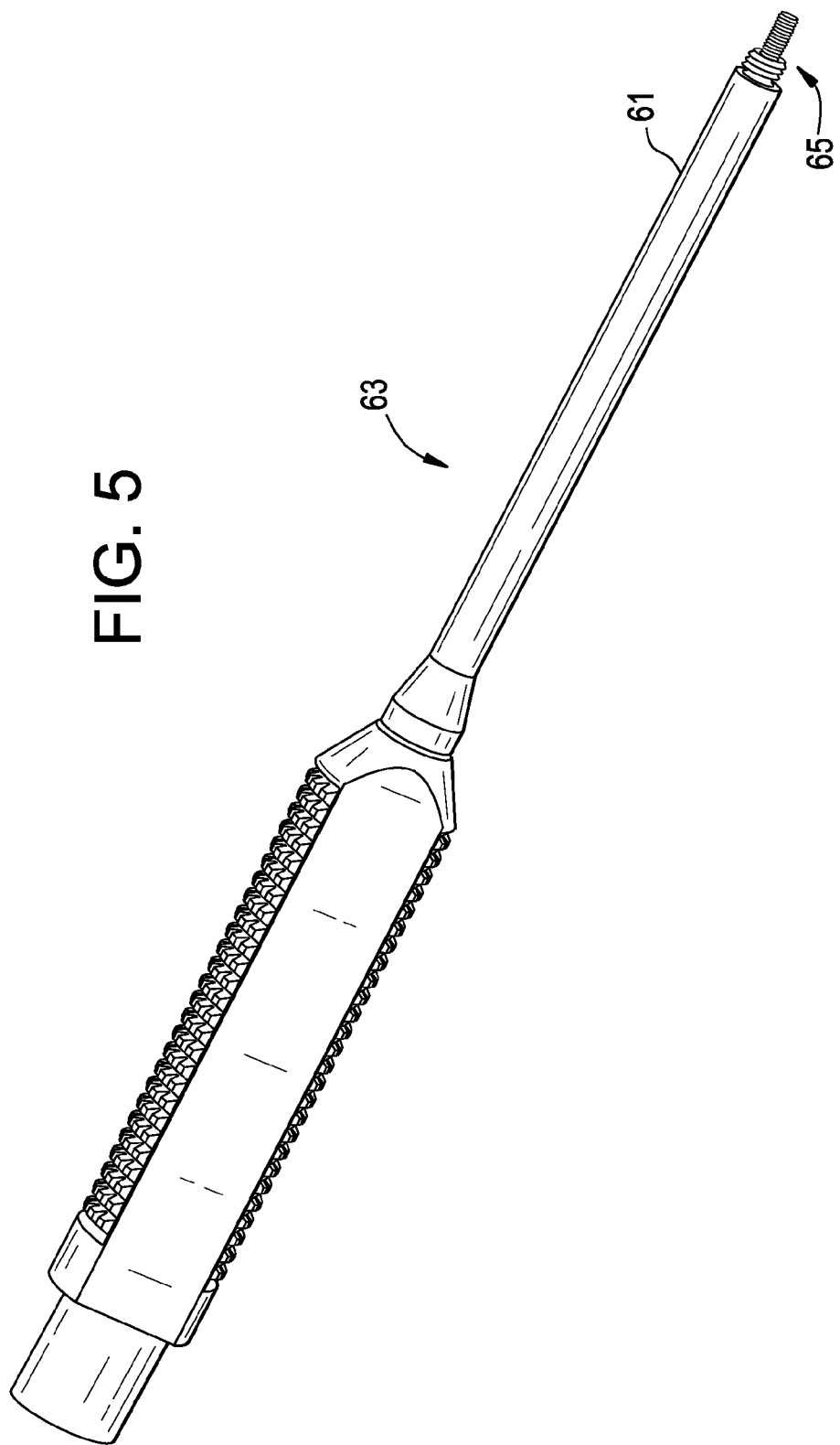
FIG. 5 is a perspective view of an inserter component of the present invention.
Figure 6:
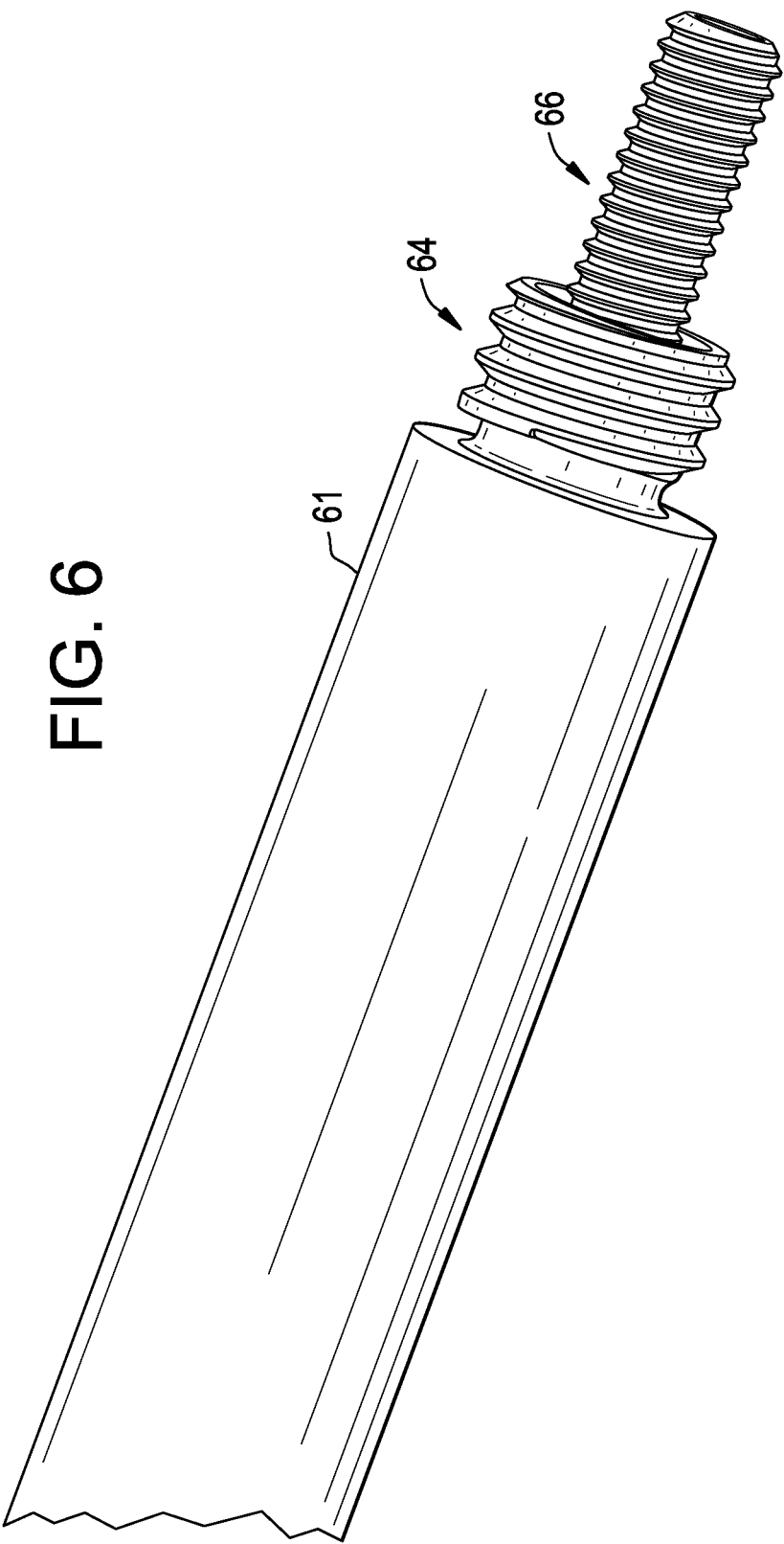
FIG. 6 is a perspective view of a distal portion of an inserter component of the present invention.
Figure 7:
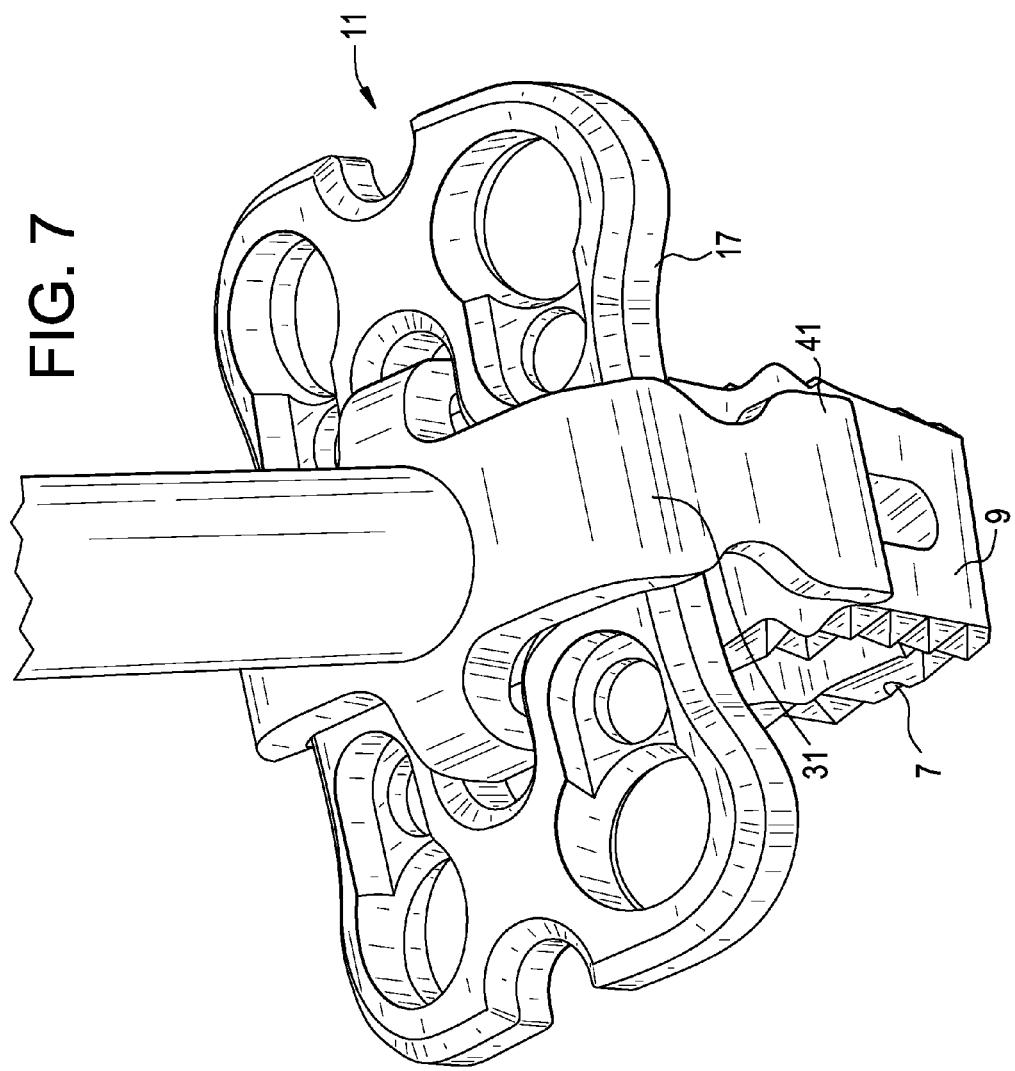
FIG. 7 is a perspective view of an assembly of the present invention loaded onto the inserter of the present invention.

Now referring to FIGS. 1-10, there is provided an assembly comprising:
- a) a spinal interbody implant 1 having a proximal wall 3 having a recess 5, a distal wall 7 and a pair of lateral walls 9 connecting the proximal and distal walls, and a central through-hole 10,
- b) a spinal plate 11 having a proximal surface 13, a distal surface 15, a pair of lateral walls 17, and a central window 19 extending from the proximal surface to the distal surface, the central window having an inner surface 21,
- c) an alignment clip 23 having a base 25 having an upper surface 27, a lower surface 29, a pair of side surfaces 31 connecting the upper and lower surfaces, a proximal surface 33 and a distal surface 35, a central through-hole 37, a first pair of arms 39 extending respectively from the upper and lower surfaces of the clip, a second pair of arms 41 extending respectively from the side surfaces of the clip, and an annulus 43 extending distally from the central-throughhole of the clip;

wherein the spinal plate is disposed between the proximal wall of the spinal interbody implant and the distal surface of the clip, wherein the first pair of arms are respectively received in the central window of the spinal plate and contact the inner surface of the central through-hole, and wherein the second pair of arms respectively contact the pair of lateral walls of the spinal implant, and wherein the second pair of arms respectively contact the pair of lateral walls of the spinal plate, wherein each arm of the second pair of arms has a projection extending therefrom, and wherein the projection contacts the distal surface of the spinal plate, wherein the annulus of the clip is received in and extends through the central window of the plate, and wherein the annulus of the clip contacts the proximal wall of the implant.

When a distal end portion of the inserter is placed in the assembly, it passes through the central through-hole of the base of the clip, the annulus of the clip, and the central window of the plate in order to connect with the recess in the proximal wall of the implant.

Therefore, in accordance with the present invention, there is provided an assembly comprising:
- a) a spinal interbody implant having a proximal wall having a recess, a distal wall and a pair of lateral walls connecting the proximal and distal walls,
- b) a spinal plate having a proximal surface, a distal surface, a pair of lateral walls, and a central window extending from the proximal surface to the distal surface, the throughhole having an inner surface
- c) an alignment clip having a base having an upper surface, a lower surface, a pair of side surfaces connecting the upper and lower surfaces, a proximal surface and a distal surface, a central through-hole, a pair of arms extending respectively from the side surfaces, and an annulus extending distally from the central-throughhole of the clip;

wherein the spinal plate is disposed between the proximal wall of the spinal interbody implant and the distal surface of the clip, wherein the pair of arms respectively contact the pair of lateral walls of the spinal interbody implant, wherein the pair of arms respectively contact the pair of lateral walls of the spinal plate, wherein the annulus of the clip is received in an extends through the central window of the spinal plate, and wherein the annulus of the clip contacts the proximal wall of the spinal interbody implant.

Also in accordance with the present invention, there is provided an assembly comprising:
- a) a spinal interbody implant having an upper surface, a proximal wall, a distal wall and a pair of lateral walls connecting the proximal and distal walls,
- b) a spinal plate having a proximal surface, a distal surface, a pair of lateral walls, and a central window extending from the proximal surface to the distal surface, the window having an inner surface
- c) a clip having a base having an upper surface, a lower surface and a pair of side surfaces connecting the upper and lower surfaces, a proximal surface and a distal surface, a first pair of arms extending respectively from the upper and lower surfaces and a second pair of arms extending respectively from the side surfaces;

wherein the spinal plate is disposed between the proximal wall of the spinal interbody implant and the distal surface of the clip, wherein the first pair of arms are respectively received in the window of the spinal plate and contact the inner surface of the window, and wherein the second pair of arms respectively contact the pair of lateral walls of the spinal interbody implant, and wherein the second pair of arms respectively contact the pair of lateral walls of the spinal plate.

Also in accordance with the present invention, there is provided an assembly comprising:
- a) a spinal interbody implant having a proximal wall, a distal wall and a pair of lateral walls connecting the proximal and distal walls,
- b) a spinal plate having a proximal surface, a distal surface, a central window therebetween, a pair of lateral walls;
- c) a clip having a base having an upper surface, a lower surface, a proximal surface, a distal surface, a central throughhole between the proximal and distal surfaces, a pair of side surfaces connecting the upper and lower surfaces, a pair of arms extending respectively from the side surfaces, and a central annulus extending from the distal surface;

wherein the spinal plate is disposed between the proximal wall of the spinal interbody implant and the distal surface of the clip, wherein the second pair of arms of the clip respectively contact the pair of lateral walls of the spinal interbody implant, and wherein the central annulus of the clip extends through the central window of the plate to abut against the proximal wall of the spinal interbody implant.

Also in accordance with the present invention, there is provided a spinal alignment clip having a base having an upper surface, a lower surface, a pair of side surfaces connecting the upper and lower surfaces, a proximal surface and a distal surface, a central through-hole, a first pair of arms extending respectively from the upper and lower surfaces and a second pair of arms extending respectively from the side surfaces, and an annulus extending distally from the central-throughhole of the clip.

In some embodiments, the central annulus of the clip distally extends past the distal surface of the plate. In this condition, the clip creates a gap between the interbody implant and the plate, thereby allowing the interbody implant to be recessed in the vertebral body (approximately up to 4 mm). This also allows the plate to be positioned along the anatomical shape of the spine in the lateral plane.

Figure 12:
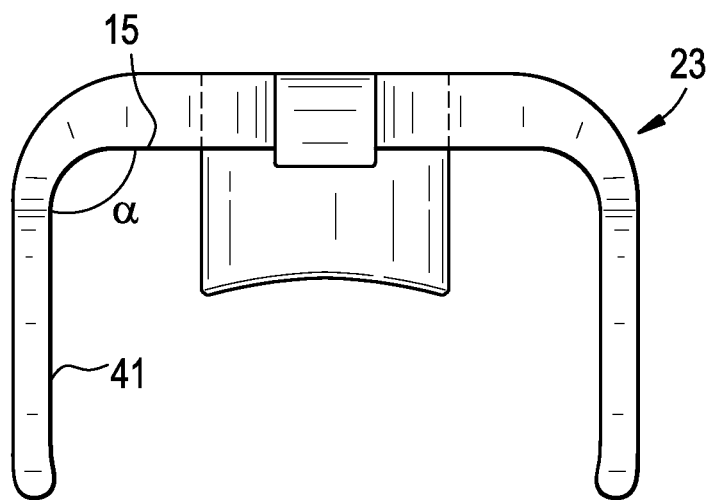
FIG. 12 is a top view of a clip of the present invention.

In some embodiments, as in FIG. 12, each of the arms and the distal surface of the clip form an angle a of less than 90 degrees (in some embodiments, between 85 degrees and 89 degrees. This slightly-less-than perpendicular angle produces a spring effect that allows these arms to clasp the interbody implant.

In some embodiments, each of the second pair of arms has a projection 51 extending therefrom so that each projection can contact the distal surface of the plate. This contact insures that the proximal surface of the plate lies flat against the distal surface of the base of the clip.

Figure 11:
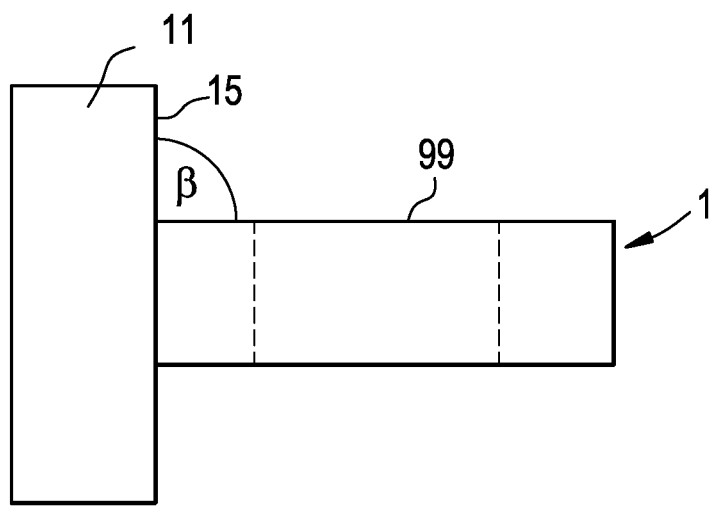
FIG. 11 is a side view of a plate-cage assembly.

In some embodiments, as in FIG. 11, the distal surface of the plate and the upper surface 99 of the cage can form an angle β therebetween of between 85 degrees and 95 degrees. This particularizes the desired alignment of the cage and plate. Preferably, the angle β is between 88 and 92 degrees.

Figure 8:
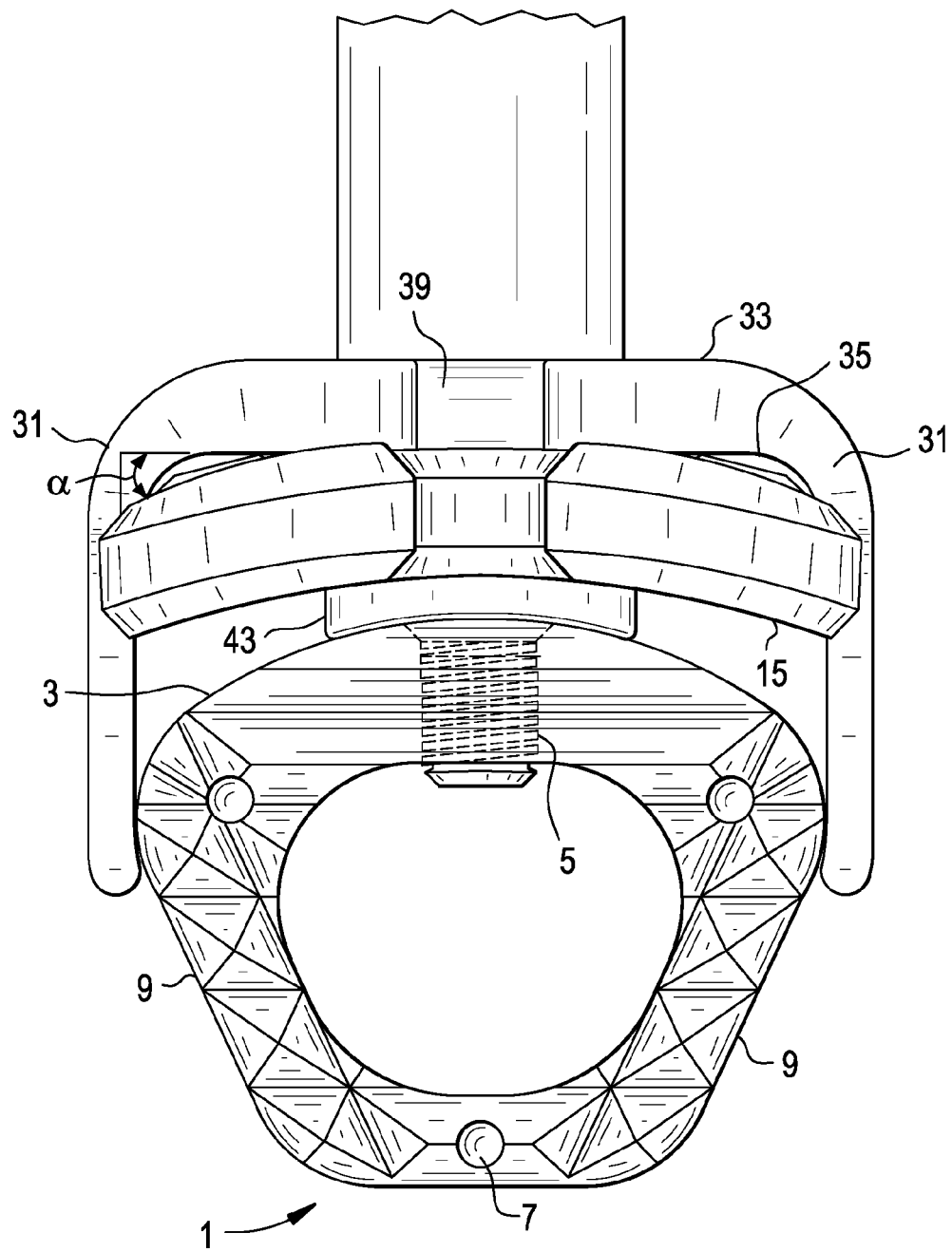
FIG. 8 is a top view of an assembly of the present invention loaded onto the inserter of the present invention.
Figure 9:
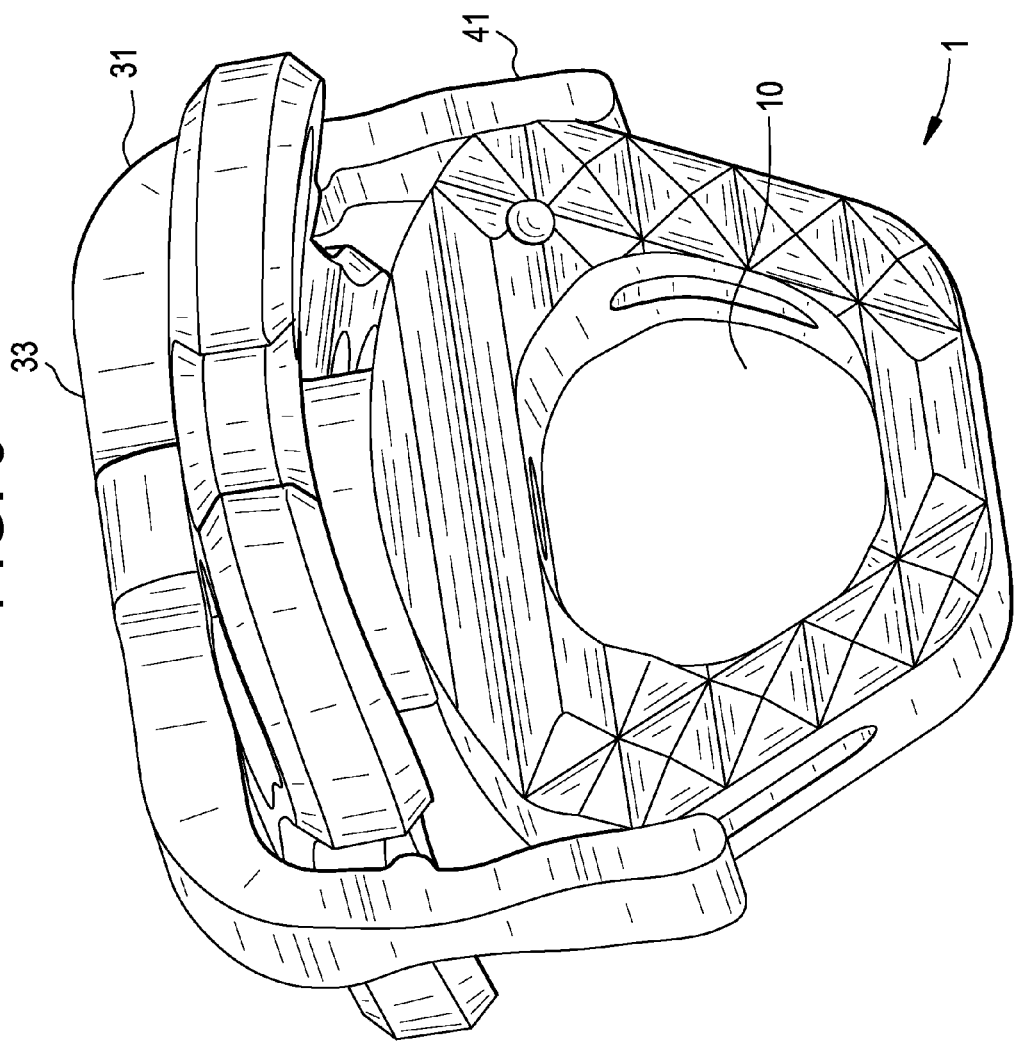
FIGS. 9-10 are perspective views of an assembly of the present invention.
Figure 10:
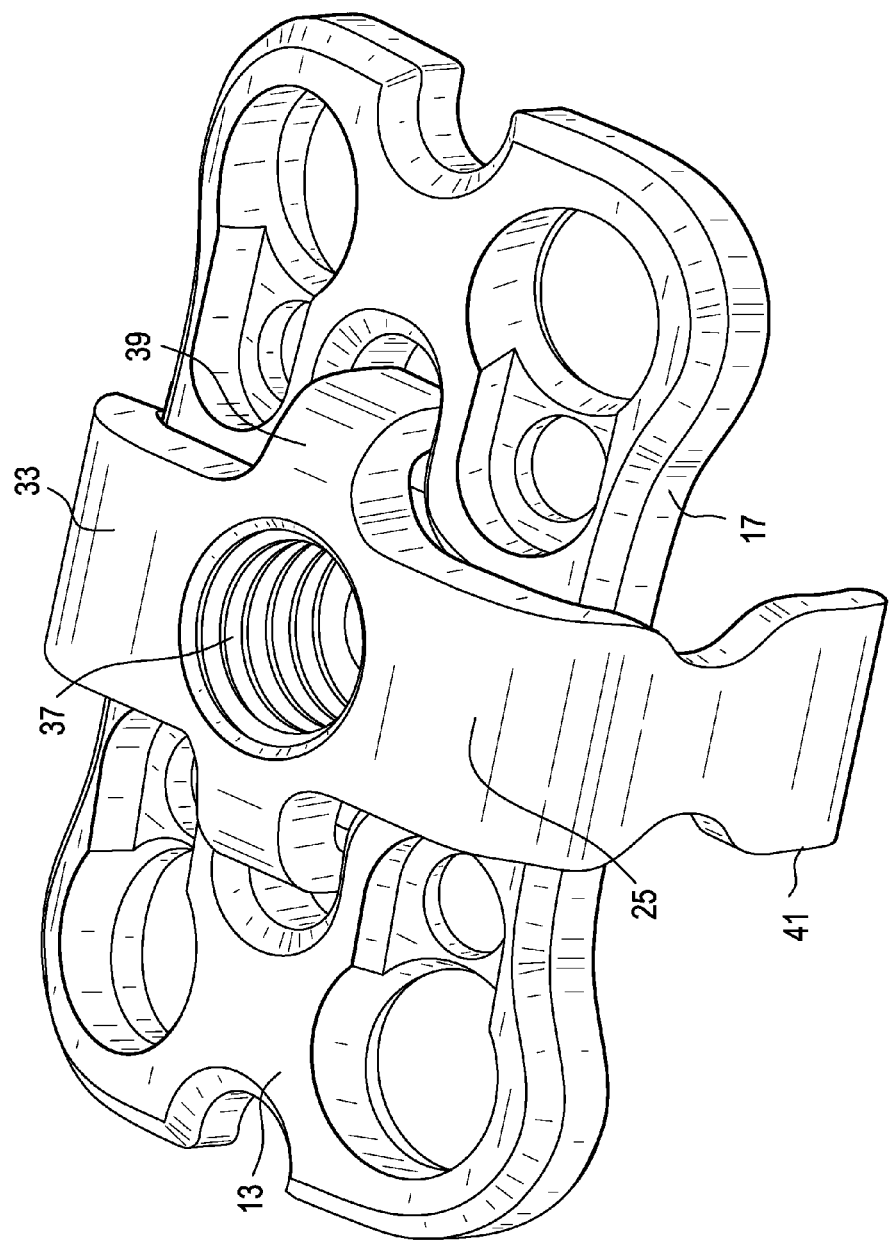

In use, the surgeon assembles the implant, plate and clip as shown in FIGS. 8-10, so that:
  a) the first pair of arms are respectively received in the central though-hole of the spinal plate and contact the inner surface of the central through-hole,
  b) the second pair of arms respectively contact the pair of lateral walls of the spinal implant,
  c) the second pair of arms respectively contact the pair of lateral walls of the spinal plate.
  d) each arm of the second pair of arms has a projection extending therefrom, and wherein the projection contacts the distal surface of the spinal plate,
  e) the annulus of the clip is received in an extends through the central through-hole of the plate, and
  f) the annulus of the clip contacts the proximal wall of the implant.

Next a distal end portion 61 of the inserter 63 is placed in the assembly so that it passes through the central throughhole of the base of the clip, the annulus of the clip, and the central through-hole of the plate and connects with the recess in the proximal wall of the implant. The inserter is then rotated so that the thread 65 on the distal end portion of the inserter threadably mates with the threads on the clip and implant, thereby securing the assembly and providing the desired alignment of the interbody implant and the plate. Inserter thread 65 comprises a proximal large diameter thread 64 (which mates with a thread on the clip) and a distal small diameter thread 66 (which mates with a thread on the implant).

Next, the assembly is placed into the spine so that the interbody implant is fit into an intervertebral disc space and the plate abuts the adjacent vertebral bodies.

Next, bone screws are passed throughhole the screwholes of the plate to secure the plate to the adjacent vertebral bodies.

Lastly, the inserter is unthreaded and removed from the assembly.

In embodiments in which the full clip-plate-implant assembly is implanted in a single insertion step (as above), it is not necessary for the inserter to have the large diameter thread 64.

In another embodiment of using the invention, a discectomy is performed, the endplates are shaped, distraction is performed and the disc space is trialed. Next, just the spinal implant (such as a cage) is implanted into the disc space. The distraction is then released and the instruments removed. Next, the plate-clip assembly (which is held together by the inserter) is implanted.

In embodiments in which the cage is first inserted alone and then the clip-plate- assembly is implanted in a subsequent insertion step, it is necessary for the inserter to have the large diameter thread 64.

In some sequential-implantation embodiments, the surgeon first inserts the implant by itself into the interbody space so that the interbody implant is fit into an intervertebral disc space.

Figure 13B:
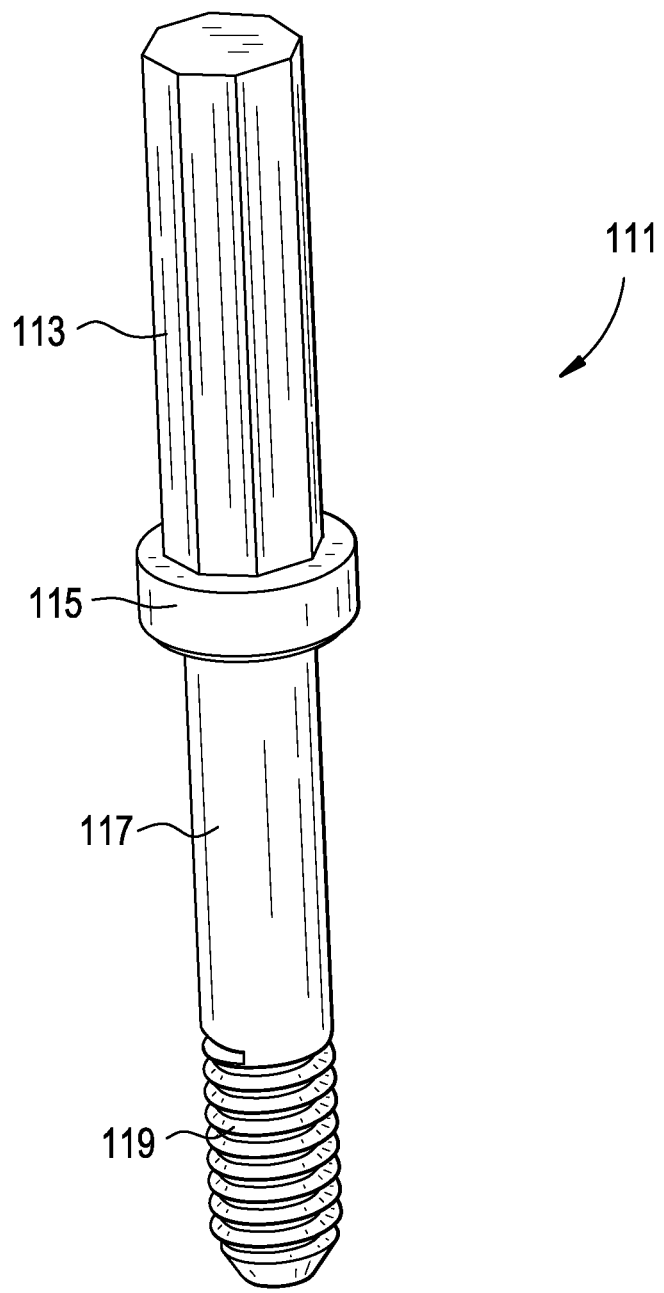
Figure 13H:
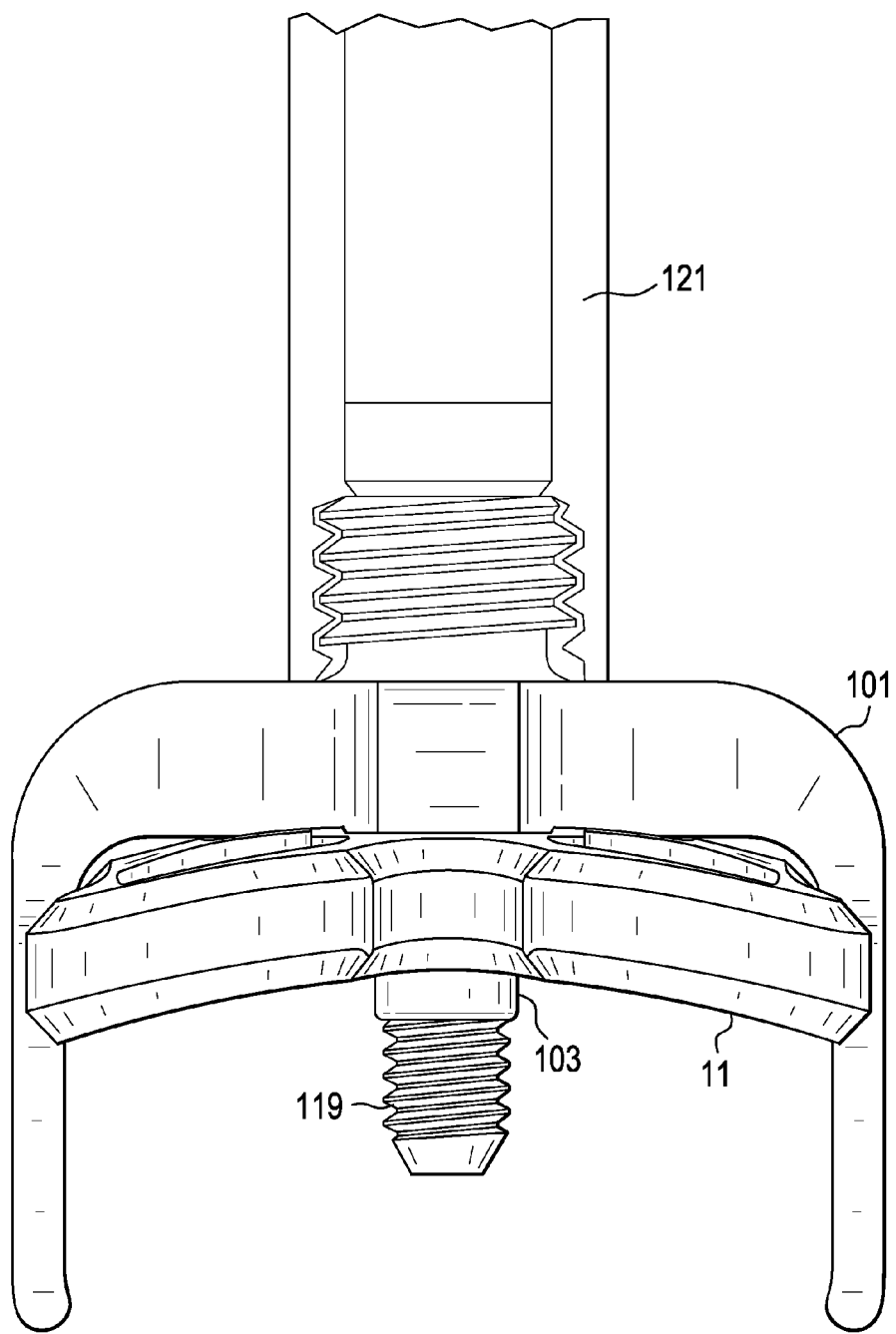

Next, and now referring to FIG. 13*a*, the surgeon or assistant assembles the temporary fixation screw 111 to the distal bore 124 of the inner shaft 123 of inserter 63. As shown in FIG. 13*b*, the temporary fixation screw 111 has a proximal shaft 113, an intermediate ring 115 extending therefrom, and a distal shaft 117 having a threaded tip 119. Next, the surgeon prepares to affix this assembly to the clip 101. In these embodiments, and now referring to FIGS. 13*c* and *d*, the clip 101 is substantially the same as that shown previously, but also has a threaded annulus 105 extending from the proximal face of the clip. In addition, the central annulus 103 extending from the distal face of the clip has an elongated shape.

Next, the outer shaft 121 of inserter 63 is then connected to the alignment clip 101 (FIGS. 13*e* and *f*) by threadably mating the distal end portion of the outer shaft 121 to the threaded annulus 105 of the clip. Outer shaft 121 has a distal inner thread (not shown) that mates with threaded annulus 105 of the clip.

Next, the surgeon or assistant assembles the plate and clip as shown in FIG. 13*g* and *h*, so that:
  a) the first pair of arms are respectively received in the central though-hole of the spinal plate 11 and contact the inner surface of the central through-hole,
  b) the second pair of arms respectively contact the pair of lateral walls of the spinal plate 11.
  c) each arm of the second pair of arms has a projection extending therefrom, and wherein the projection contacts the distal surface of the spinal plate 11,
  d) the annulus 103 of the clip 101 is received in and extends through the central through-hole of the plate.

Figure 13I:
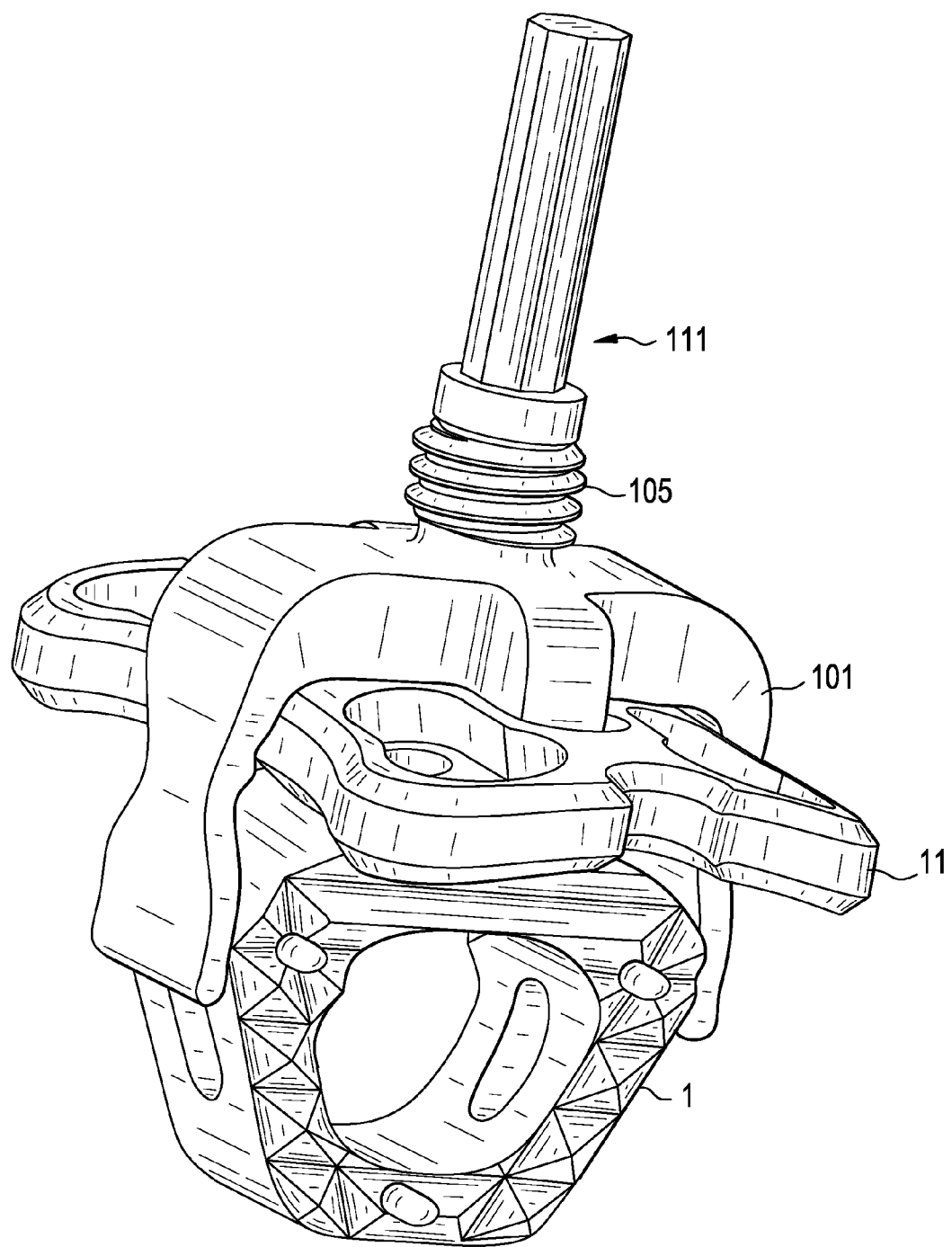
Figure 13J:
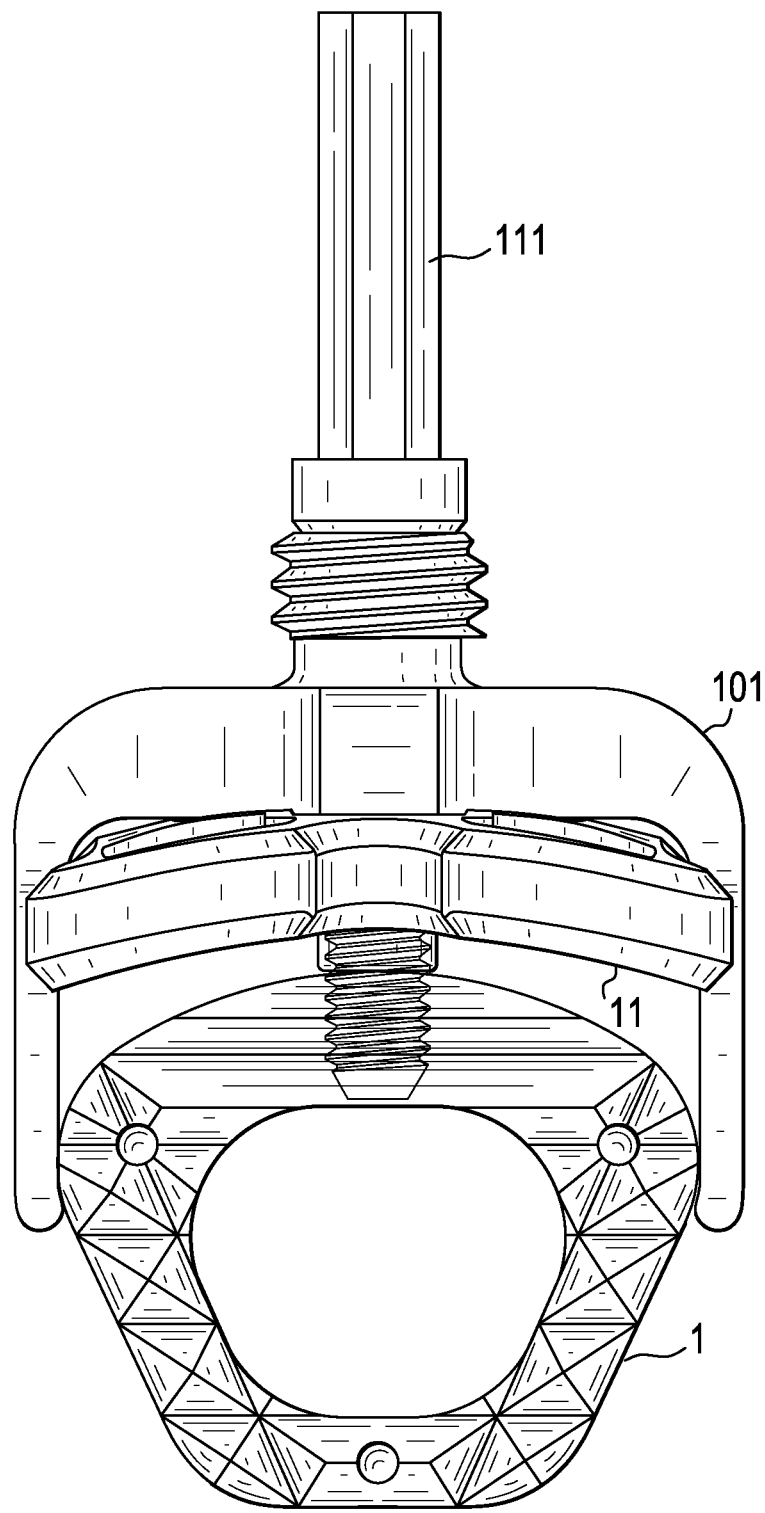

Next, as in FIGS. 13*i* and *j*, the surgeon positions the inserter/clip/plate assembly into the spine and connects the assembly to the implant so that:
  a) the distal threaded tip 119 of the temporary fixation screw 111 threadably mates to the implant and the central through-hole of the plate, and connects with the recess in the proximal wall of the implant;
b) the second pair of arms respectively contact the pair of lateral walls of the spinal implant 1, thereby securing the assembly and providing the desired alignment of the interbody implant and the plate.
c) the annulus 103 of the clip contacts the proximal wall of the implant 1.
d) the plate 11 abuts the adjacent vertebral bodies.

Next, the outer shaft portion of the inserter is removed from alignment clip by unthreading the outer shaft while keeping the inner shaft in place. Once the outer shaft is unthreaded, the surgeon will gently remove the inner shaft portion of the inserter, leaving the temporary fixation screw connected to the clip/plate/implant and thus retaining the plate's desired aligned position.

Next, bone screws are passed through the screwholes of the plate to secure the plate to the adjacent vertebral bodies.

Next, the temporary fixation screw is unthreaded and removed from the assembly.

Lastly, the alignment clip is removed from the plate.

The interbody implant of the present invention can be made from any conventional structural biocompatible material, such as metals (such as titanium alloy, cobalt-chrome, stainless steel, and polymers. In some embodiments, the interbody implant is a cage made from a composite comprising:
a) 40-99% polyarylethyl ketone PAEK, and
b) 1-60% carbon fiber
wherein the polyarylethyl ketone PAEK is selected from the group consisting of polyetherether ketone PEEK, polyether ketone ketone PEKK, polyether ketone ether ketone ketone PEKEKK,and polyether ketone PEK.

Preferably, the carbon fiber is chopped. Preferably, the PAEK and carbon fiber are homogeneously mixed. Preferably, the composite consists essentially of PAEK and carbon fiber. Preferably, the composite comprises 60-80 wt % PAEK and 20-40 wt % carbon fiber, more preferably 65-75 wt % PAEK and 25-35 wt % carbon fiber. In some embodiments, the cage is made from materials used in carbon fibers cages marketed by DePuy Synthes Spine, Raynham, Mass., USA. In some embodiments, the composite is PEEK-OPTIMA™, available from Invibio of Greenville, N.C..

In other embodiments, the cage is made from a metal such as titanium alloy, such as Ti-6A1-4.

In other embodiments, the cage is made from an allograft material.

In some embodiments, the cage is made from ceramic, preferably a ceramic that can at least partially be resorbed, such as HA or TCP. In other embodiments, the ceramic comprises an oxide such as either alumina or zirconia.

In some embodiments, the cage is made from a polymer, preferably a polymer that can at least partially be resorbed, such as PLA or PLG.

In some embodiments, the cage is provided in a sterile form.

In some embodiments, autologous bone graft material obtained from the iliac crest of the human patient is inserted into the chamber of the cage.

In other embodiments, bone graft material made from allograft particles such as cancellous chips and demineralized bone matrix may be used.

In other embodiments, concentrated osteoinductive materials such as autologous platelet rich plasma or recombinant growth factors may be used.

In other embodiments, concentrated osteogenetic materials such as autologous mesenchymal stem cells (MSCs) or recombinant MSCs may be used.

In preferred embodiments, the interbody implant is the BENGAL™ cage, available from DePuy Synthes spine in Raynham, Mass., USA).

The plate of the present invention can be made from a biocompatible metal, such as titanium alloy, cobalt-chrome or stainless steel. In preferred embodiments, the plate is SKYLINE™ plate, available from DePuy Synthes spine in Raynham, Mass., USA).

The clip of the present invention can be made from a biocompatible structural material such as a metal, such as titanium alloy, cobalt-chrome or stainless steel.

We claim:
1. An assembly comprising:
a) a spinal interbody implant having a proximal wall having a recess, a distal wall and a pair of lateral walls connecting the proximal and distal walls,
b) a spinal plate having a proximal surface, a distal surface, a pair of lateral walls, and a central window extending from the proximal surface to the distal surface, the throughhole having an inner surface; and
c) an alignment clip having a base having an upper surface, a lower surface, a pair of side surfaces connecting the upper and lower surfaces, a proximal surface and a distal surface, a central through-hole, a pair of arms extending respectively from the side surfaces, and an annulus extending distally from the central-throughhole of the clip;
wherein the spinal plate is disposed between the proximal wall of the spinal interbody implant and the distal surface of the clip,
wherein the pair of arms respectively contact the pair of lateral walls of the spinal interbody implant,
wherein the pair of arms respectively contact the pair of lateral walls of the spinal plate,
wherein the annulus of the clip is received in an extends through the central window of the spinal plate, and
wherein the annulus of the clip contacts the proximal wall of the spinal interbody implant.

2. The assembly of claim 1 further comprising:
d) an inserter comprising a proximal handle and a distal end portion, wherein the distal end portion passes through the central through-hole of the base of the clip, the annulus of the clip, and the central window of the spinal plate and connects with the recess in the proximal wall of the spinal interbody implant.

3. The assembly of claim 1 wherein each of the arms and the distal surface of the clip form an angle a of less than 90 degrees.

4. The assembly of claim 1 wherein each arm has a projection extending therefrom, and wherein the projection contacts the distal surface of the spinal plate.

5. The assembly of claim 1 wherein the central annulus of the clip distally extends past the distal surface of the spinal plate.

6. An assembly comprising:
a) a spinal interbody implant having an upper surface, a proximal wall, a distal wall and a pair of lateral walls connecting the proximal and distal walls,
b) a spinal plate having a proximal surface, a distal surface, a pair of lateral walls, and a central window extending from the proximal surface to the distal surface, the window having an inner surface, and
c) a clip having a base having an upper surface, a lower surface and a pair of side surfaces connecting the upper and lower surfaces, a proximal surface and a distal surface, a first pair of arms extending respectively from the upper and lower surfaces and a second pair of arms extending respectively from the side surfaces;
wherein the spinal plate is disposed between the proximal wall of the spinal interbody implant and the distal surface of the clip,
wherein the first pair of arms are respectively received in the window of the spinal plate and contact the inner surface of the window, and
wherein the second pair of arms respectively contact the pair of lateral walls of the spinal interbody implant, and
wherein the second pair of arms respectively contact the pair of lateral walls of the spinal plate.

7. The assembly of claim 6 wherein each arm of the second pair of arms has a projection extending therefrom, and wherein the projection contacts the distal surface of the spinal plate.

8. The assembly of claim 6 wherein each of the second pair of arms and the distal surface of the clip form an angle α of less than 90 degrees.

9. The assembly of claim 6 wherein the distal surface of the plate and the upper surface of the interbody implant form an angle β therebetween of between 85 degrees and 95 degrees.

10. The assembly of claim 6 wherein the distal surface of the plate and the upper surface of the interbody implant form an angle β therebetween of between 88 degrees and 92 degrees.

11. The assembly of claim 6 wherein each of the second pair of arms has a projection extending therefrom, and wherein the projection contacts the distal surface of the spinal plate.

12. An assembly comprising:
   a) a spinal interbody implant having a proximal wall, a distal wall and a pair of lateral walls connecting the proximal and distal walls,
   b) a spinal plate having a proximal surface, a distal surface, a central window therebetween, a pair of lateral walls,
   c) a clip having a base having an upper surface, a lower surface, a proximal surface, a distal surface, a central throughhole between the proximal and distal surfaces, a pair of side surfaces connecting the upper and lower surfaces, a pair of arms extending respectively from the side surfaces, and a central annulus extending from the distal surface;

wherein the spinal plate is disposed between the proximal wall of the spinal interbody implant and the distal surface of the clip,
wherein the second pair of arms of the clip respectively contact the pair of lateral walls of the spinal interbody implant, and
wherein the central annulus of the clip extends through the central window of the plate to abut against the proximal wall of the spinal interbody implant.

13. The assembly of claim 12 wherein the proximal wall of the spinal interbody implant has a recess, the assembly further comprising:
   d) an inserter having a proximal handle and a distal portion having a tip,
wherein the distal portion of the inserter passes through the central throughhole and central annulus of the clip and the central window of the plate so that the tip contacts the recess of the implant.

14. The assembly of claim 12 wherein each arm of the clip has a projection extending inwardly therefrom, and wherein the projection contacts the distal surface of the spinal plate.

15. A spinal alignment clip having a base having an upper surface, a lower surface, a pair of side surfaces connecting the upper and lower surfaces, a proximal surface and a distal surface, a central through-hole, a first pair of arms extending respectively from the upper and lower surfaces and a second pair of arms extending respectively from the side surfaces, and an annulus extending distally from the central-throughhole of the clip.

16. The clip of claim 15 wherein each arm of the second pair of arms has a projection extending inwardly therefrom.

17. The clip of claim 15 wherein each arm of the second pair of arms forms an angle α with the distal surface of the clip of between 85 degrees and 89 degrees.

18. The clip of claim 15, attached to a spinal plate having a proximal surface, a distal surface, a pair of lateral walls, and a central window extending from the proximal surface to the distal surface, the window having an inner surface,
wherein the annulus of the clip is received in the central window of the plate.

* * * * *